(12) United States Patent
Boehm et al.

(10) Patent No.: US 7,488,605 B2
(45) Date of Patent: Feb. 10, 2009

(54) METHOD FOR CHARACTERIZING AND SEPARATING MOLECULAR ASSOCIATES

(75) Inventors: Gerald Boehm, Halle (DE); Ulrich Schmidt, West Leederville (AU)

(73) Assignee: ACGT ProGenomics AG, Halle (Saale) (DE)

( * ) Notice: Subject to any disclaimer, the term of this patent is extended or adjusted under 35 U.S.C. 154(b) by 0 days.

(21) Appl. No.: 10/950,347

(22) Filed: Sep. 23, 2004

(65) Prior Publication Data

US 2005/0069935 A1    Mar. 31, 2005

Related U.S. Application Data

(63) Continuation of application No. 10/129,313, filed as application No. PCT/EP00/10877 on Nov. 3, 2000, now abandoned.

(30) Foreign Application Priority Data

Nov. 3, 1999    (DE) ................... 199 52 955

(51) Int. Cl.
    *G01N 33/566* (2006.01)
(52) U.S. Cl. .................... 436/501; 424/204.1
(58) Field of Classification Search ............... 424/9.1, 424/184.1, 204.1; 435/4, 5
    See application file for complete search history.

(56) References Cited

U.S. PATENT DOCUMENTS

| 5,540,494 A | 7/1996 | Purvis, Jr. et al. |
| 5,811,653 A | 9/1998 | Turpen |
| 6,498,017 B2 | 12/2002 | Riesner et al. |

FOREIGN PATENT DOCUMENTS

| DE | 19952955.8 | * 11/1999 |
| EP | 0 627 626 A1 | 12/1994 |
| WO | WO 93/04194 A1 | 3/1993 |
| WO | WO 97/04311 A2 | 2/1997 |
| WO | WO 99/08695 A1 | 2/1999 |
| WO | WO 99/15903 A1 | 4/1999 |
| WO | WO 99/57566 A1 | * 11/1999 |

OTHER PUBLICATIONS

Goldmann, C. et al. "Packaging of Small Molecules into VP1-Virus-Like-Particles of the Human Polyomavirus JC Virus," *J. of Virol. Meth.* 2000, pp. 85-90, vol. 90.
Palutke, M. et al. "Flow Cytometric Purification of Alzheimer's Disease Amyloid Plaque Core Protein Using Thioflavin T," *Cytometry* 1987, pp. 494-499, vol. 8.
Petenate, A.M. and Glatz, C.E. "Isoelectric Precipitation of Soy Protein. II. Kinetics of Protein Aggregate Growth and Breakage" *Biotechnol. Bioeng.* 1983, pp. 3059-3078, vol. 25, No. 12.
Wall, J. and Solomon, A. "Flow Cytometric Characterization of Amyloid Fibrils," *Meth. in Enzymol,* 1999, pp. 460-466, vol. 309.
Marie et al.; "Enumeration of Marine Viruses in Culture and Natural Samples by Flow Cytometry"; 1999, *Applied and Environmental Microbiology*, vol. 65, No. 1, pp. 45-52.
Saltzman, W. Mark et al.; "Antibody Diffusion in Human Cervical Mucus"; 1994, *Biophysical Journal*, vol. 66, pp. 508-515.
Hercher, M. et al., "Detection and Discrimination of Individual Viruses by Flow Cytometry," *The Journal of Histochemistry and Cytochemistry*, 1979, pp. 350-352, vol. 27, No. 1, USA.
Marie, D., et al., "Enumeration of Marine Viruses in culture and Natural Samples by Flow Cytometry," *Applied and Environmental Microbiology*, Jan. 1999, pp. 45-52, vol. 65, No. 1.
Steen, H., "Flow Cytometric Studies of Microorganisms," *Flow Cytometry and Sorting, Second Edition*, 1990, pp. 605-622, Wiley-Liss, Inc.

* cited by examiner

*Primary Examiner*—Stacy B Chen
(74) *Attorney, Agent, or Firm*—Townsend and Townsend and Crew LLP

(57) ABSTRACT

The present invention relates to a method for characterising and optionally separating molecular associates, especially particles having a size smaller than 300 nm. Partial units of the molecular associates are used as markers, whereby said units are marked with fluorescent dyes. The marked associates and aggregates are characterised by means of a FACS (fluorescence-activated cell sorter).

7 Claims, 7 Drawing Sheets

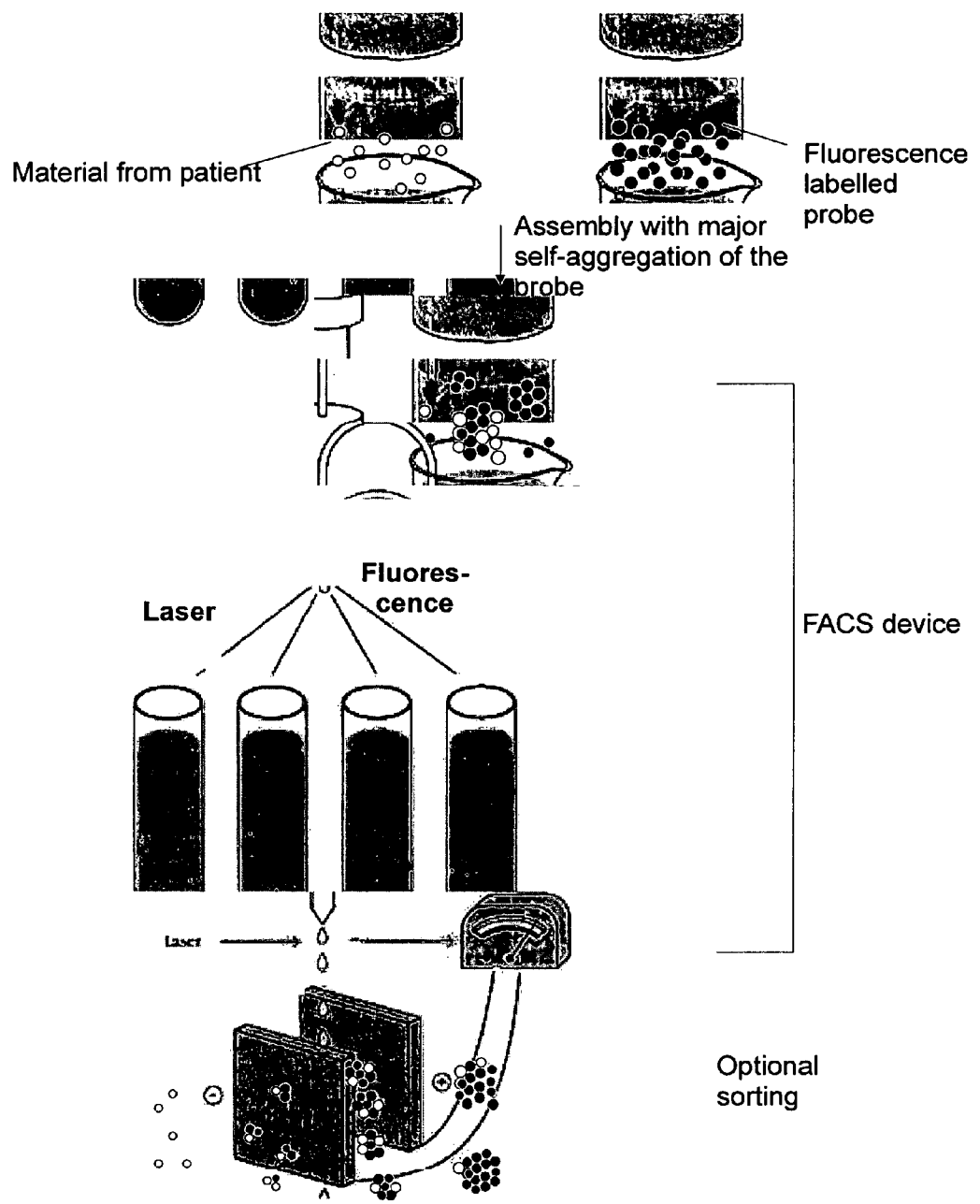
Figure 1. Principle of the measurement.

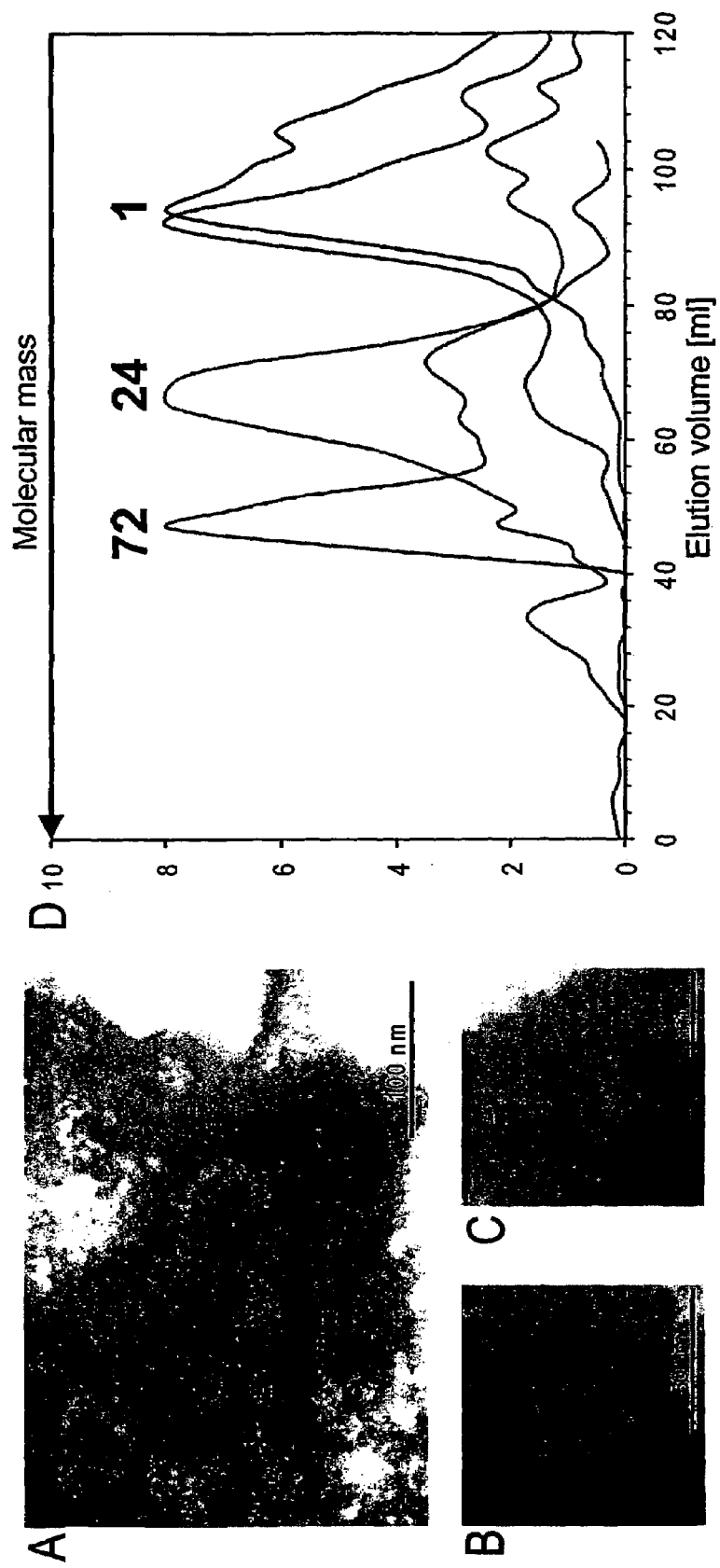
Figure 2. Characterization of virus-like capsids.

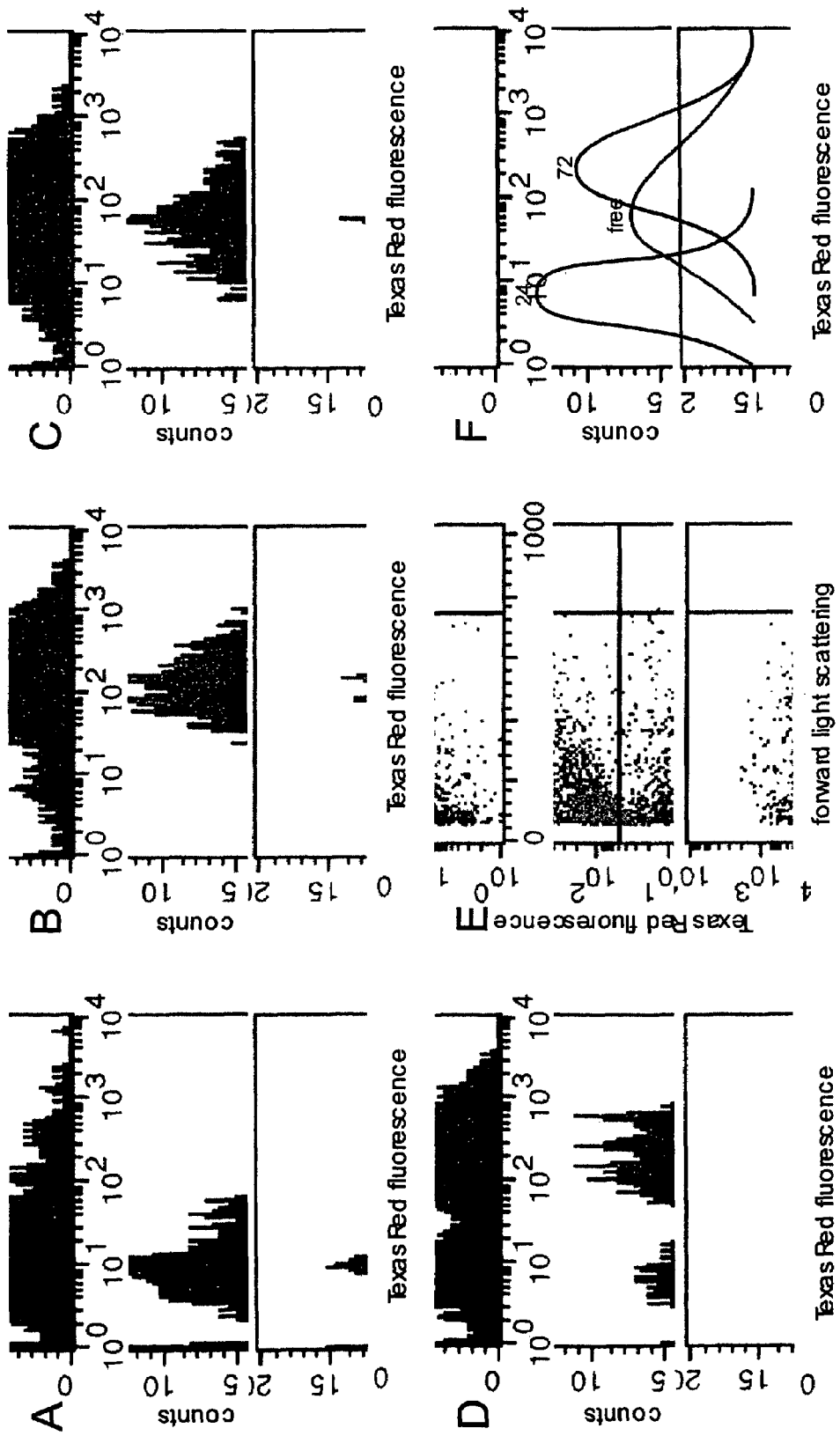
Figure 3. FACS analysis of TexasRed labelled virus particles.

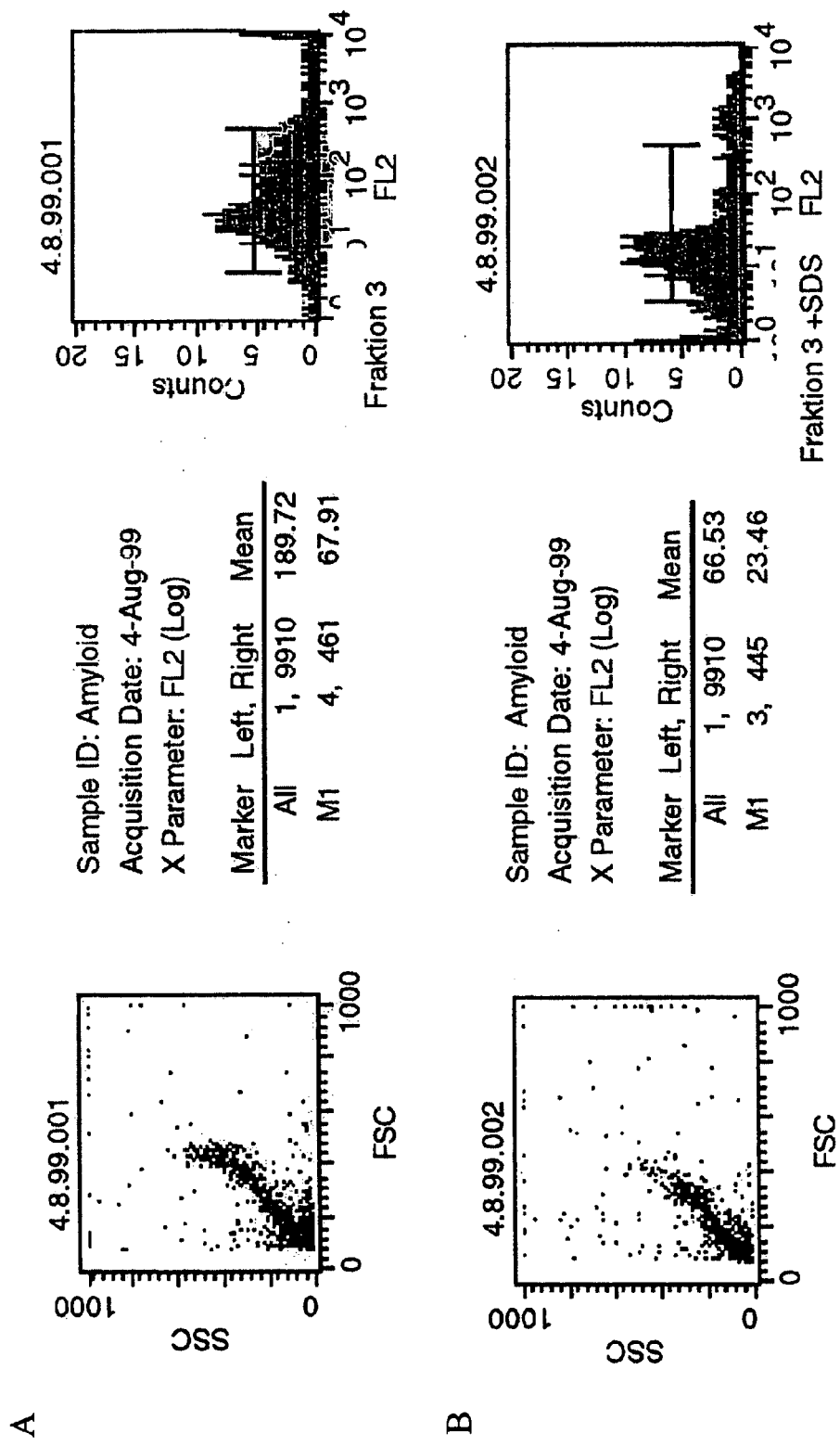
Figure 4a,b. FACS analysis of amyloidogenic aggregates of the Alzheimer peptide.

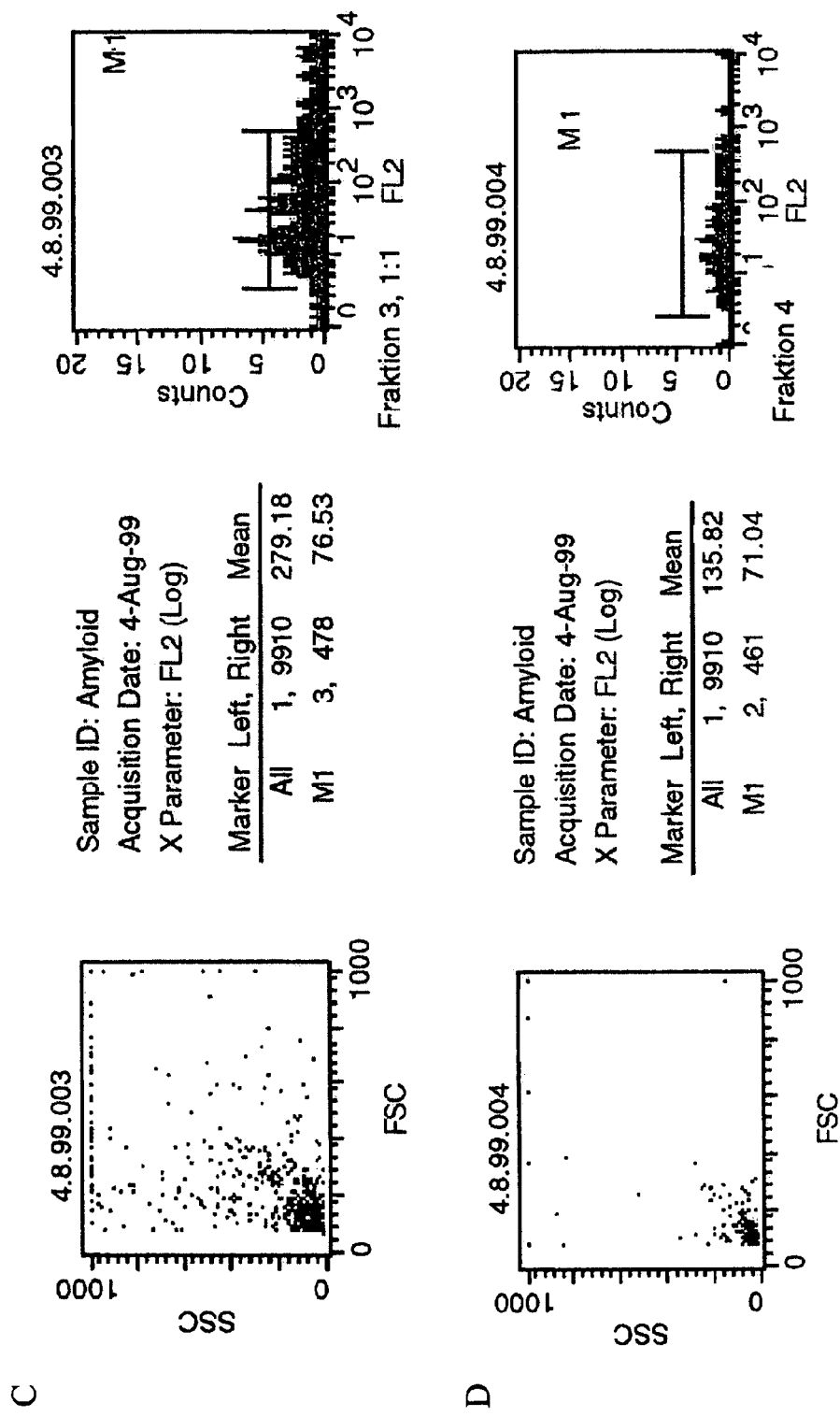
Figure 4c,d. FACS analysis of amyloidogenic aggregates of the Alzheimer peptide.

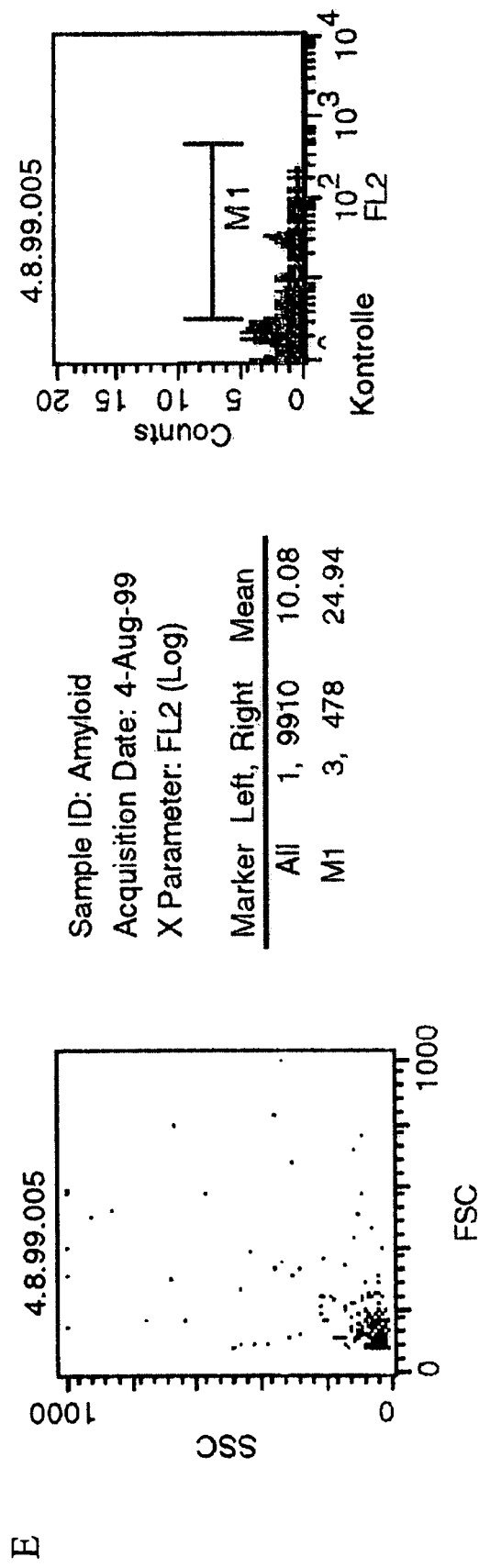
Figure 4e. FACS analysis of amyloidogenic aggregates of the Alzheimer peptide.

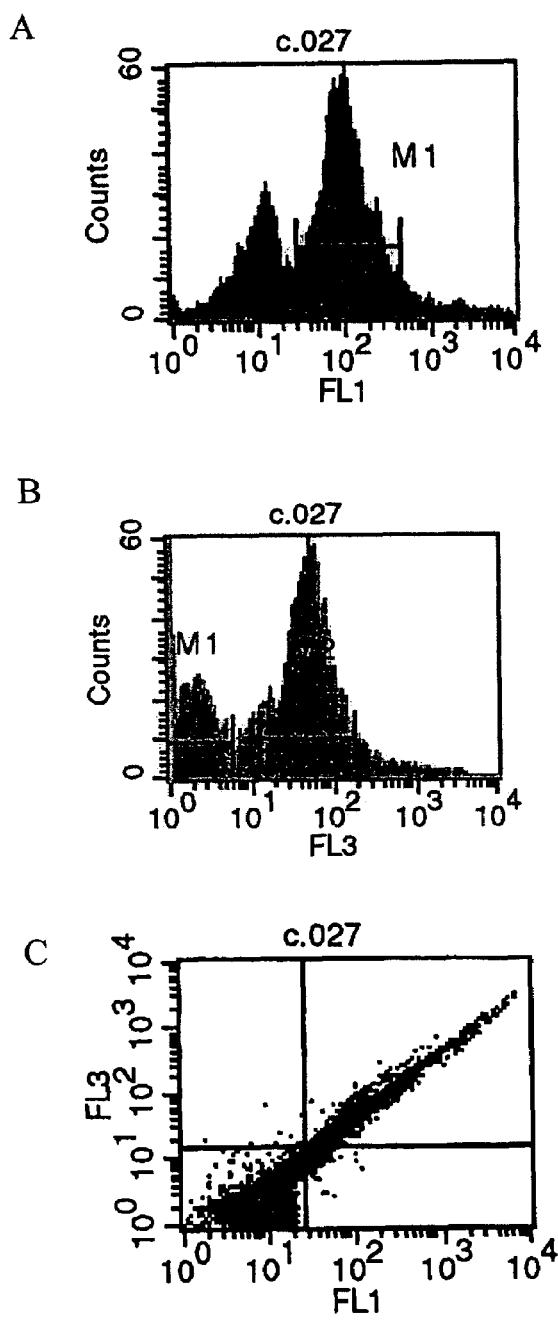
Figure 5. FACS analysis of mixed-assembly virus-like particles with two fluorescence dyes.

METHOD FOR CHARACTERIZING AND SEPARATING MOLECULAR ASSOCIATES

This application is a continuation of U.S. patent application Ser.No. 10/129,313, filed Oct. 31, 2002, now abandoned, which is the national phase under 35 U.S.C. §371 of PCT/EP00/10877, filed Nov. 3, 2000, which claims priority to Germany patent application No. 199 52 955.8, filed Nov. 3, 1999.

The present invention relates to a method for the characterization and alternatively for the separation of molecular associates, in particular for particles of a size smaller than 300 nm, whereby subunits from these molecular associates labelled with fluorescent dyes are used as markers and the labelled associates or aggregates are characterized by means of a FACS (Fluorescene-Activated Cell Sorter) device.

FIELD OF INVENTION AND STATE OF THE TECHNOLOGY

In a series of diseases, morphological "irregular associates", so-called aggregates, are formed. Such pathological deposits often consist of proteins, protein fragments, or peptides, which are distributed throughout the body (systemically) or are found in concentrated form in particular organs like the pancreas or the central nervous system. In Alzheimers disease, a peptide (Alzheimer β peptide, length mostly 42 amino acids, as a fragment of a larger precursor protein) is found as a characteristic deposit of the brain, forming the so-called amyloidogenic aggregate ("senile plaques"). As a second hallmark of the Alzheimers disease the formation of neurofibrillary structures ("tangles" or "paired helical filaments") occurs which are formed by the tau protein. So far it has not been conclusively clarified for many amyloidogenic diseases in which way these protein deposits alter the course of the disease, and whether these deposits are causally responsible for the disease or are merely side effects.

A similar picture is shown in the transmissible spongiform encephalopathies which are caused by the prion protein. The human form of the disease is manifested in the Creutzfeld-Jacob-disease; in animals, the diseases of the cattle (BSE) and sheep (scrapie) are particularly well-known. A possible connection between the occurrence of BSE in cattle and a new form of the Creutzfeld-Jacob-Disease (vCJD) is currently not excluded (M. E. et al., *Transmissions to mice indicate that 'new variant' CJD is caused by the BSE agent*, Nature 389, S. 498-501, 1997). For the similar disease of the sheep (scrapie) a connection has been observed between the concentration of disease relevant proteins and the infectivity. The following table has been taken from, altered and extended, from Kelly, J. W., *Alternative conformations of amyloidogenic proteins govern their behavior*, Curr, Opin. Struct. Biol. 6, S. 11-17, 1996.

Predominantly Neurodegenerative Amyloidogenic Diseases:

| Disease | Participating protein |
| --- | --- |
| Alzheimers disease | β protein/Alzheimer β peptide (1-40, 1-42, 1-43); tau protein |
| Transmissible Spongiform Encephalopathy (CJD, Kuru, BSE, Scrapie) | prion protein |
| Chorea Huntington | Huntingtin |
| Parkinsons disease | Synuclein |
| Hereditary Cerebral Amyloidal Angiopathy | cystatin C |

Other amyloidogenic diseases:

| Disease | Participating protein |
| --- | --- |
| Injectional localized Amyloidosis | Insulin |
| β-2 Microglobulin Amyloidosis | β-2-microglobulin |
| Primary Asystemic Amyloidosis | Immunglobulin |
| Finnish Hereditary Systemic Amyloidosis | Gelsolin |
| Atrial Amyloidosis | atrial natriuretic factor |
| Familial Amyloid Polyneuropathy | Transthyretin |
| Medullary carcinoma of the thyroid | Calcitonin |
| Hereditary Non-Neuropathic Amyloidosis | Lysozyme |
| Diabetes mellitus Type II | islet amyloid polypeptid |
| Reactive Asystemic Amyloidosis | Lipoproteins |
| Cleidocranial Dysplasy | transcription faktor CBFA1 |
| Hereditary Renal Amyloidosis | Fibrinogen |
| Ocular pharyngetic myodystrophy | poly(A) binding protein II |

The aggregates observed in these diseases are formed mainly from the proteins cited or from fragments of these proteins, and are each very characteristic for the occurrence of the diseases. Potential diagnostic methods for these diseases can therefore be based on the fact that the proteins, respectively the protein fragments, meaning subunits of the molecular associates, have the tendency for a selective aggregation respective association in vitro under appropriate conditions. In most cases of these diseases it has been difficult so far to find a diagnostic assay or a technical solution therefore. Hitherto, known test methods for the diagnosis of Alzheimers disease are based on an immunological detection of the participating proteins and peptides, and are therefore not based on a direct detection of the associates respectively of the aggregated deposits or their subunits. Cerebrospinal fluid (CSF, liquor) is taken for this from the patient by a painless lumbar puncture. The substances to be detected for the Alzheimers disease are contained in this CSF. The precise detection is obtained by simultaneously measuring the two soluble Alzheimer-specific substances, tau protein and amyloid β peptide (M. Shoji et al., *Combination assay of CSF tau, Aβ1-40 and Aβ1-42(43) as a biochemical marker of Alzheimer's disease*, J. Neurol. Sci. 158, S. 134-140, 1998; F. Hulstaert, K. Blennow, A. Ivanoiu, H. C. Schoonderwaldt, M. Riemenschneider, P. P. De Deyn, C. Bancher, P. Cras, J. Wiltfang, P. D. Mehta, K. Iqbal, H. Pottel, E. Vanmechelen, and H. Vanderstichele: *Improved discrimination of AD patients using beta-amyloid(1-42)and tau levels in CSF*, Neurology 52, S. 1555-1562, 1999).

In the U.S. Pat. No. 5,593,846 a method for the determination of the concentration of the soluble amyloid β peptides is described, however, the pathological component (deposits) is not detected hereby.

In the U.S. Pat. No. 5,434,050 a diagnostic method for Alzheimers disease is described, where a peptide is fixed to a solid structure (for example material from a brain biopsy). Such a method can not be carried out without a serious medical intervention and is not used at the moment.

In Patent WO 99/15903 a method is described where pathological deposits can be detected using the FCS method (Fluorescence Correlation Spectroscopy). However, the FCS method is diffusion controlled and technically unsuitable for high throughput, only a small number—to a maximum of 2 to 3 molecular species of different sizes—are distinguished; with the species having to have masses differing at least tenfold and the distribution of sizes can only be estimated, and where during each step of the method only few types (usually one) of fluorescence dyes can be used. The self-aggregation of the probe is a significant problem of this method. Therefore, this method is unsuitable to clearly capture a broad spectrum of possible pathological signals and characteristics, in particular a simultaneous detection of P peptide and tau protein is not possible. Furthermore, a considerable amount of time is required for each measurement. The method developed here shows no influence of self-aggregation of the probe on the results, since these self-aggregates can be distinguished on the basis of the properties of the light scattering and the fluorescence intensity of heterogeneous associates. The possibility of self-aggregation of the probe, excluded in the above mentioned application, is useful for the present method since in this case an optimal sensitivity is achieved. Patent WO 99/15903 also describes a diagnostic method for the determination of pathological protein deposits, based upon formation of aggregates with suitable probes; similar to the method described in patent WO 99/15903, a generalized measurement of sample-probe-associates is claimed, the invention described uses the measurement of the protein aggregates by means of flow cytometry as an advantage compared to the current state of technology. However, in the present invention as well as in patent WO 99/15903 molecular associates are characterized, although the descriptions make clear that these can be pathological deposits. Furthermore, in Patent WO 99/15903 the measurement of an associate is performed by determining a probe towards a target, with the probe and the target being defined as the same compounds/structures. Here, it is open according to claim 1 if the probe is labelled or not. In the invention described here subunits/partial structures of the associates are also associated with other subunits, but with the difference that the probes have to be labelled with a fluorescence dye. This characteristics is also shown in patent WO 99/15903, therefore representing the state of technology. In claim 1 of patent WO 99/15903 is—as a further essential characteristics—a limitation of time indicated in which the association of the probe with the target is measured, before the self-aggregation of the probe predominates. This time limit does not occur in the present invention and due to this, the present invention is considerably distinguished from the method described in Patent WO 99/15903. Moreover, the detection respectively the characterization of the associates is even advantageously ensued at the moment and under the condition of the self-aggregation of the probe. This fundamental feature, however, is not fulfilled in Patent WO 99/15903. In relation to the measurement using FACS, the method here described is new and in addition promises a higher diagnostic reliability regardless of the self-aggregation of the probe, also inventive in accordance with the patent acts. The inventors from patent WO 99/15903 were seemingly aware of the disadvantage that the measurement has to be done before self-aggregation predominates.

The U.S. Pat. No. 5,486,460 describes a method for Alzheimer diagnosis in which higher concentrated cerebrospinal fluid is dried and afterwards labelled with Thioflavin S. However, this method is extremely unattractive in practice and also insufficiently specific for a clinical diagnosis; it has been disregarded.

The Patent WO 97/04311 A2 claims a FACS-based method for the isolation of living cells from a mixture of a variety of living cells, differing in presence and distribution of receptors on their surfaces. In advantage to the state of the technology no fluorescence-labelled anti-bodies, demanding a permeabilization and therefore a killing of the cells, are used, but fluorescence-labelled peptides deduced from natural ligands of receptors existing on the cell surface are used. By incubation of the cells with such peptides they are settling at their respective receptors and thereby mark a specific cell population that can be isolated using a FACS device. This method differs therefore fundamentally from the present invention, since the diagnostic method described here uses florescence-labelled peptides exclusively for the characterization of protein aggregates and not for cell populations. The processes and intention for analysis are entirely different. In the patent application presented here, an isolation of the protein aggregates by a FACS can be performed optionally. However, sorting of particles that are as small as the protein aggregates described here is not explained in patent WO 97/04311 A2. Although claim 6 of the patent WO 97/04311 A2 contains, among others, a fluorescence-labelled amyloid-β-peptide, no dependence of the invention presented here occurs, since there is no incubation of cells or interaction of the fluorescence-labelled peptide with cellular receptors at any time. In addition, the FACS technology in this invention is primarily used for the analysis of protein aggregates, while the patent WO 97/04311 A2, on the other hand, describes a method for the separation of living cells.

In the Patent U.S. Pat. No. 5,540,494 a method is described which allows the calculation of the absolute radius and the absolute surface of the particles analyzed, using data measured with a conventional flow cytometer. However, according to the present invention, the interpretation of the data, i.e. the FACS-based measurement of the characteristics of the protein aggregates, is performed without using the method claimed in that particular patent. It is further not necessary to determine absolute dimensions of the protein aggregates, since the flow cytometer is calibrated with a suitable standard before the measurement occurs and all data measured are related to that standard.

In any case it would be very desirable to develop a highly specific and sensitive method, allowing the peptides (protein fragments) related to the diseases mentioned before, to be detected in soluble form or also in form of deposit-forming seeds for crystallization, and therefore to have a clear and sensitive diagnostic assay for the respective disease. It would further be of immense advantage to gain as early as possible a correct (biochemical, serological) diagnosis of the disease, allowing first therapeutic steps before the outbreak of the disease to be taken. An early diagnostics, combined with a successful following therapy would therefore lead to immense savings within the health service. Additionally, such a diagnostic assay could also be used regularly as a medical check-up on healthy respectively unsuspicious persons of progressed age as a preventive action.

The purpose of the invention presented here is, therefore, to provide a method for the characterization of molecular associates, lacking the already mentioned drawbacks of the current state of the technology.

According to the invention this is achieved by a method described in claim 1 for the characterization of molecular associates, consisting of subunits, whereby:

non-associated subunits are labelled with at least one fluorescence dye, the labelled subunits are brought into contact with each other or with unlabelled subunits, or with molecular associates consisting of subunits, in order to reach a deposition and/or a binding of the labelled subunits to each other or to unlabelled subunits, or molecular associates consisting of subunits, and to form labelled molecular associates, the labelled associates are characterized through a FACS (Fluorescence-Activated Cell Sorter), and the molecular associates are separated optionally by well-known methods.

Beneficial ways of application of the invention arise from the sub-claims as well as the description.

DESCRIPTION

In biochemical, biotechnological and medical diagnostic assays the problem arises commonly to characterize associates of molecular structures. The subunits of the associates can hereby belong to different chemical classes, like peptides respectively proteins, glycoproteins, nucleic acids, lipids and phospholipids, carbohydrates and polysaccharides as well as substances derived thereof, or the associates can also contain subunits from different classes. These characterizations are relevant for medical diagnosis or for therapeutic use. Also, in the field of the bioscientific and biochemical basic research as well as in applied research such characterizations can be necessary.

In the invention described here an unexpected experimental result is used to measure and characterize such molecular associates as well as to separate an ensemble of such associates with respect to selected properties like size or composition.

Surprisingly, it was found that the characterization of molecular associates can be solved by a method developed for the characterization and sorting of cells in the first place. The equipment used in this respect is therefore called FACS device (Fluorescence-Activated Cell Sorter). A FACS device (a cell sorter, in a simpler version also called a flow cytometer) is simplified an optical measuring device which analyses the scattered light signals and fluorescence signals of individual particles in a single drop focused in a liquid stream. In contrast to a static fluorimeter, these results are based on a simultaneous measurement of more than one physical parameter of each particle, passing the detecting system in a fluid stream. The optical excitation is performed by a laser. The evaluation is carried out after counting a statistically significant amount of single events (particles) in a liquid stream. Cell sorting devices (FACS equipment) offers in comparison to flow cytometers the additional choice to provide each drop of the liquid stream containing particles with an electrical charge according to its measured properties such as fluorescence intensity or scattered light (size and form respectively granularity of the particle), which then can be used to sort the particles into different containers. The charged drop containing the particles is hereby lead through an electrical field and is separated according to its charge.

FACS equipment allows quantitative measurements of individual particles with high precision. They offer in particular the option to analyze a large amount of particles in a very short time. A further advantage is that the particles can be characterized on a preparative scale, due to the option to sort the particles for certain predefined properties (for example size or fluorescence intensity). In the FACS equipment the analysis of a particle within a liquid stream is primary carried out with regard to its light scattering signals and fluorescence signals.

Until now in the current state of the technology only systems with cells or organella have been measured by FACS. Surprisingly, it could be shown that using FACS equipment, preferable FACS devices of the newest generation, single molecular associates and aggregates can also be characterized. According to the invention, these associates can be much smaller than the given resolving limit of such equipment (ca. 300 nm). By using suitable fluorescence dyes effects within the solution occur that allows the molecular substances to be characterized in size and structure with a high reproducibility. Any fluorescence dye which emits a sufficiently intense fluorescence signal for the detection of the associates after the formation of the molecular associates can be used for this purpose. Dyes with a high quantum efficiency are preferred when the sensitivity of the method has to be high. Simultaneously with the laser-based method it is possible to gain information about the form and the granularity based on the lateral scattering as well as information about the size of the molecular associates and aggregates on the basis of the forward scattering.

The invention described here offers a method for the characterization of molecular associates. The molecular associates can consist of chemically different or similar subunits, which are associated either specifically or unspecifically. According to the invention, non-assembled subunits of the molecular associates are provided in this method with at least one optical marker, in particular with at least one fluorescent molecule. These labelled subunits are then brought as "marker" into contact with each other or with unlabelled subunits or with molecular associates consisting of subunits, in order to reach an association and/or a binding of the labelled subunits together with unlabelled subunits or with molecular associates consisting of subunits. In this way, labelled molecular associates are formed, which then can be characterized with respect to size, form and composition using a FACS (Fluorescence-Activated Cell Sorter). Subsequently, optionally a separation of the associates investigated can be carried out with known methods, for example a separation of the molecular associates due to their sizes or their fluorescence intensity. Associates having a certain pre-selected property (size, signal intensity) are electrically charged by the FACS. By using this electrical charge of the associate, a separation (sorting) can be performed. Other methods of separation are known by the expert and can be used depending on the chemical or physical structure of the molecular associates. After the separation, a further characterization of the sorted associates can follow, for example by optical methods such as measuring the fluorescence intensity, fluorescence spectroscopy, light scattering, absorption spectroscopy, and/or with respect to the circular dichroitic or the linear dichroitic properties or the scattered light distribution of the molecular associates. Since the characterization by FACS is carried out in a flow-through system, the separation of the molecular associates can follow immediately after the FACS characterization.

During the characterization by FACS more than one dye can be measured simultaneously. Therefore, it is possible to distinguish between several different subunits of a molecular associate, by using different fluorescence dyes for the labelling of different subunits of the molecular associates.

With the characterization according to the invention it is possible on one hand to make judgements about the structure of the associate and the aggregates themselves (for example by the labelling of different subunits of an associate or an aggregate with different fluorescence dyes). By using different fluorescence dyes for different subunits several different subunits of the molecular associates can be distinguished according to the invention. The present state of the technology of the equipment allows the differentiation of up to 4 different subunits of the molecular associates. On the other hand, it is also possible to analyze the population distribution of associates or aggregates, i.e. to make a distribution analysis of size and form of the individual aggregates and associates in the suspension or solution.

A self-association of the fluorescence labelled substance, without inclusion of the unlabelled substance contained in the test solution (for example, liquor from the patient), can be distinguished by the method described from the case where by desire the unlabelled substance of the test solution is included in the associates. This is achieved by a comparative analysis of the molecular mass and the form of the aggregates (using the scattered light portion of the FACS signal) as well as the measurement of the fluorescence intensity of the aggregates in relation to them. Comparing the multi-parametrical data measurements with suitable selected reference standards allows to distinguish the self-aggregation of the fluorescence labelled probe, i.e. a measuring artifact from a certain measurement by analyzing the portion of non-fluorescence-labelled substances in the measured aggregate.

According to the invention, two forms of molecular associates are distinguished. On the one hand, associates are analyzed, leading to regular geometrical structures with a mainly homogeneous population. Such associates are defined in this invention as "regular" molecular associates, respectively, as molecular associates with three-dimensional or stoichiometrical structure; they are built up by specific association processes. Examples for such molecular associates are virus or phage coats (cf. the following section), which are sometimes built from only one type of subunits and often have an icosahedral structure, or macromolecular associates built from heterogeneous subunits, like ribosomes, chaperone complexes or proteasomes. On the other hand and according to the invention molecular associates are included which can have a statistical distribution in size and structure and which consist of regular associates not at all or mostly. These molecular associates are called aggregates according to the invention, or molecular associates irregular in relation to their structure and/or composition. Such aggregates appear, for example, during the recombinant production of proteins in the form of inclusion bodies, or they are pathological characteristics of diseases in the form of amyloidogenic plaques, inclusion bodies, or other morphological structures. They are usually variable in size and structure. In this invention the simplified terminus "molecular associates" is chosen as a generally characterizing term for both forms of the association which are not restricted with respect to their regularity.

The method used in the present description allows, for example, the characterization of regular molecular associates. Such associates can be found for instance in viral coat structures, which in many cases are formed icosahedrally. Other viruses or phages are of non-icosahedral symmetry; they are, for example, filamentous, helical, or have other morphological forms of arrangement. The coats of viruses and phages normally have a defined structure, with subunits precisely oriented towards each other, and therefore they are good model systems for macromolecular associates with regular composition and/or structures. A characterization of the size as well as the molecular composition for each single virus coat can be an important analytical aid for the characterization of these virus shells as well as for other molecular associates (like cellular proteasomes, chaperon-complexes, or ribosomes). Examples of such viruses and phages, in the order of their primary morphology, are listed in the following:

| Morphology | Representative (virus resp. phage) |
|---|---|
| Amorphous resp. unknown | Umbravirus; Tenuivirus |
| bacilliform | Baculoviridae; Badnavirus; Barnaviridae; Filoviridae; Rhabdoviridae |
| filamentous | Capillovirus; Carlavirus; Closterovirus; Furovirus; Inoviridae; Lipothrixviridae; Potexvirus; Potyviridae; Tobamovirus; Tobravirus; Polydnaviridae |
| helical | Hordeivirus; Paramyxoviridae; Trichovirus |
| icosahedral | Adenoviridae; Astroviridae; Birnaviridae; Bromoviridae; Caliciviridae; Caulimovirus; Circoviridae; Comoviridae; Corticoviridae; Dianthovirus; Enamovirus; Hepadnaviridae; Herpesviridae; Idaeovirus; Iridoviridae; Lviviridae; Luteovirus; Machlomovirus; Marafivirus; Microviridae; Necrovirus; Nodaviridae; Papovaviridae; Partitiviridae; Parvoviridae; Phycodnaviridae; Picornaviridae; Reoviridae; Rhizidiovirus; Sequiviridae; Sobemovirus; Tectiviridae; Tetraviridae; Tombusviridae; Totiviridae; Tymovirus |
| isometric | Cystoviridae; Geminiviridae |
| oval | Poxviridae |
| pleomorphic | Coronaviridae; Hypoviridae; Plasmaviridae |
| spherical | Arenaviridae; Arterivirus; Bunyaviridae; Flaviviridae; Orthomyxoviridae; Retroviridae; Togaviridae |
| lemon-shaped | Fuselloviridae |
| phage with tail extension | Myoviridae; Podoviridae; Siphoviridae |

An example of such viral shell structures is demonstrated in the following using the Polyomavirus pseudocapsid (from VP1 subunits of the Polyomavirus protein envelope). In the examples shown in the table above the SSV1-particle (Fuselloviridae) must be emphasized, which infects the archaebacterium *Sulfolubus shibatae*. This representative of a phage is hyperthermophilic due to its host specificity, therefore stable at high temperatures, and can thus be useful for many applications in the field of biotechnology and medicine. It is able to form a very stable protein shell. Similar representatives can be found from the Lipothrixviridae. Not yet further classified are the thermophilic and hyperthermophilic representatives of the Bacilloviridae and the Guttaviridae, usable in processes where the stability of a protein shell (formed from the phage proteins) is relevant.

Fluorescence labellings are often carried out by specific covalent coupling of dyes to thiol groups in proteins (cysteines) and to other molecular substances. Therefore, often maleimid derivatives or iodoacetamide derivatives of fluorescence dyes are used. For the coupling to amino groups, for instance, succinimidylester, sulfonylhalide, isothiocyanates, and aldehydes are used as fluorescence marker derivates. There are more agents for the specific coupling to OH-groups (in proteins and peptides for example at serine, threonine and tyrosine), to aldehyde or ketone (for example for the labelling of polysaccharides) and to activated carboxyl groups. Specific applications could be the coupling of effector molecules with fluorescence-labelled biotin (biotinylation).

A specific fluorescence labelling of molecular substances can also be performed by non-covalent coupling. Hereby, fluorescence-labelled antibodies are used in particular, which are able due to their binding properties to bind specifically to their antigens. Especially the usage of fluorescence labelled ligands is suitable for receptors and enzymes, cofactors, substrates, or substrate analoga. Another application possibility is the use of intercalating substances, such as phenanthridynes (ethidium bromide), or acridyne and cyanine. The formation of amyloidogenic structures can be detected using the dye Congo Red, followed by a fluorescence measurement.

An important application for the invention described can be the diagnosis of amyloidogenic diseases. Biological material from the patient, for instance from homogenized tissues, liquor, blood, urine or other body fluid, is hereby mixed with one or several different fluorescence labelled protein(s) or peptide(s) (marker) and is incubated for a certain period of time. The molecular substances potentially contained in the patient's material, either in form of soluble monomeric peptides or proteins, or already in form of seeds for crystallization (primary associates) for the association process, aggregate or associate during this time specifically with the marker used. By a suitable selection of the process variables like temperature, incubation period, solvent additives, pH value and so on, and after optimization strategies and selection strategies carried out by an expert on the basis of known strategies, a differentiation of monomeric forms or of already formed associates, or of seeds for crystallization for the forming of associates can be done. Cellular factors or catalysts which also exist in the patient's test solution can contribute to the formation without disturbing the verification accuracy.

This method allows to carry out a quantitative classification of different molecular substances in one operating cycle; the relative frequency of the occurrence of associates (different types are hereby distinguishable by different fluorescence labellings) during the counting process in the FACS device is proportional to the amount of subunits which exist in the test solution (for instance patient liquor). By using different fluorescence dyes for different markers it is possible, for example, to detect in parallel the tau-protein, the Alzheimer β peptide (1-42), and the Alzheimer β peptide (1-40). At the same time it is possible by the usage of Congo Red to proof the amyloidogenic character of the aggregates formed. Modem FACS devices allow the simultaneous detection of 4 fluorescences, therefore allowing high accuracy of the diagnostics. Remarkably little test material is needed for this method, since highly sensible single-particle-measurements are carried out, which is an advantage for the patient. The multitude of possible measurement variables described before can allow precise categorization of the properties of the patients test and with this allows a good quantitative determination of the syndromes after appropriate standardization or the determination of the course and the progress of the disease.

Apart from the diagnostic usage in the field of amyloidogenic diseases, a screening of potential therapeutic substances with the described method is also possible. Here, the formation of amyloidogenic aggregates in the presence of the therapeutic substances serves as the measured variable; it can be expected that substances that prevent the formation of the amyloidogenic aggregates are also therapeutically valuable. Also, therapeutically useful could be substances which are able to dissolve the above mentioned amyloidogenic aggregates.

Apart from the use of markers which (with the exception of the fluorescence labelling) are identical with the substance attempted to detect, the use of markers that are only partly identical with the substance to be detected can be of advantage, too. Here, in particular proteins, protein fragments or peptides can be employed, which are mostly homologous to the target substance, but possess substitutions at one or more locations within the amino acid sequence. Such homologous sequences can be of advantage for the method insofar as they can possess other and often more favorable qualities for association and binding than the natural sequences. The definition of such homogeneous sequences can easily be done using the method described in the invention presented here. Furthermore, it is easy with this method to ascertain the kinetic of the forming of the aggregates and associates and with this to additionally extend the diagnostic and analytical statement of the method described. Especially in the diagnosis of amyloidogenic diseases it is therefore possible to distinguish between different kinetic phases. A fast association of additional molecules into larger aggregates or associates takes place often only after the initial (and slower) formation of a seed for crystallization. The addition of an artificial aggregation seed can therefore speed up the noticeable processes of aggregation or association.

Apart from the standardized optical and spectroscopic scopes of the FACS device it is possible, after minor technical amendments of the equipment, to separate the molecular associates by further characteristics using known separation processes, with the separated molecular associates being characterized by their optical properties or by other properties such as absorption, circular dichroitic or linear dichroitic properties, quantum efficiency, lifespan of excited aggregations, energy transfer, intensity differences, or radioactivity.

The method described in this invention permits the characterization of molecular associates of any chemical nature as well as any structure and with any ratio of mixture with the help of fluorescence labellings. The characterization is carried out by the statistical interpretation of ensembles of associates or aggregates, whereby each single associate or aggregate (particle) is measurable as a special feature. Another feature allows in parallel to the characterization the sorting and counting of the molecular particles based on important properties. Therefore, it is possible to examine the collected species with the help of other analytical methods such as electron microscopy, fluorescence microscopy, fluorescence correlation spectroscopy, etc., after the FACS analysis.

The molecular associates characterized and sorted by FACS which show particular properties can be used for further experiments (for example in cell cultures, animal models or in other tests with the need of homogeneous and qualitative valuable source material). This makes it possible with respect to desirable properties to use exactly defined and characterized molecular particles of a homogeneous population. In many cases this can be essential for the experiment.

An important advantage of the method described here is the standardization and the broad distribution of the FACS method. The technique is established in all diagnostic centers; medical test methods based on it have an important advantage in terms of infrastructure. FACS is generally performed in a flow stream, i.e. the sample to be measured runs continuously through the device. Such a flow-through system is especially suitable for automatization with respect to a high throughput screening. The equipment can be flushed quickly and automatically after every cycle of the sample, no other manual work or exchange of one-way material is necessary. The use of an autosampling device makes it possible to obtain a large sample flow rate at a workstation without substantial additional work from service personnel.

The method allows to define the quantitative ratio of its composition of different substructures for each particle, as far as these different substructures can be labelled with different fluorescence dyes. Therefore, a very precise quantification can be carried out, providing also precise statements about the statistical distribution of the composition within the population, apart from mean values for the composition. Furthermore, the particles do not necessarily need to be labelled directly; if, for instance, specific ligands or antibodies are available which bind to the substructure to be defined, an indirect labelling with fluorescence dyes can be carried out.

Finally, it is possible to analyze the molecular structure of the particles, for example with respect to the packaging efficiency of virus-like protein shells with respect to therapeutically effective substances like DNA, RNA, peptides or proteins. Such applications are for instance relevant in the area of the production of gene-therapeutical vector systems. With this, a precise analytical instrument is given to characterize and subsequently to optimize such systems.

Implementation forms of this invention are described in the following examples, which although are not meant to restrict the extent of the invention. In these examples and in the description it is referred to the following figures.

FIG. 1 shows schematically an example for the characterization of a sample by FACS. In this example, fluorescence-labelled subunits are brought together with unlabelled subunits and/or associates of a certain species to form labelled molecular associates. After excitation by a laser the signals for the size and the fluorescence are measured, allowing for a certain, pre-defined separation and sorting according to the operational principle of FACS equipment (in this case with respect to the size of aggregates or associates).

FIG. 2 shows electron microscopical photos and gel filtration analysis of virus-like capsids, characterized with the FACS technology. (A), non-assembled capsomeres, derived from the polyomavirus VP 1. (B), 45 nm particles of virus-like polyomavirus coats after dialysis at pH 7.2. (C), 30 nm particles after dialysis at pH 8.5. (D), Gel filtration tests with respect to the size distribution of the virus-like polyomavirus shells.

FIG. 3 shows the FACS analysis, belonging to FIG. 2, of Texas Red-labelled virus-like polyomavirus particles. A, analysis of the particles, consisting of 24 capsomeres. B, analysis of the association of capsids consisting of 72 pentamers. C, assembly-deficient variant PyVP1-ΔCT63. D, capsomeres under non-assembling conditions (no virus-like polyomavirus-particles). E, dot-plot of the capsomeres under non-assembling conditions. The forward light scattering is very weak due to the extremely small particle size (5 nm). F, Schematic histogram depiction of the fluorescence virus-like particles resp. of the free pentamers of different sizes.

FIG. 4 shows the results of a FACS analysis of Alzheimer β peptide (1-42) under different conditions of aggregation. A, fluorescence-labelled aggregates at 0.1 % SDS-content of the solution; B, at a SDS content of 2 % in the solvent the aggregates do not appear under otherwise identical condition; C, a mixture of fluorescence-labelled and unlabelled peptides forms aggregates under the condition of (A) with a weaker fluorescence; D, control experiment under identical conditions, using the fluorescence dye without peptide (negative control); E, control experiment under identical conditions, this time using Alzheimer β peptide (1-42), not labelled with a fluorescence dye (negative control).

FIG. 5 shows a FACS analysis of differently labelled PyVP1 variants. Capsids of PyVP1-CallsS-T249C are formed, consisting of a species labelled with Fluorescein and with Texas Red. The capsid population shows a clear Fluorescein-fluorescence (M1 in A), as well as a Texas Red-fluorescence (M2 in B). The graphing of Fluorescein-fluorescence (FL1) against Texas Red-(FL3)-fluorescence makes it obvious that both dyes are localized on one particle (upper right quadrant in C). Particles containing only one dye are not detected.

EXAMPLE 1

Production of Fluorescence-labelled Virus Coats of Defined Size and Characterization of the Virus Shells by FACS The viral coat protein in this example is the polyomavirus VP1 protein which is pentameric in solution, which according to the state of the technology can easily be assembled in vitro to a shell. Therefore, in a first step a polyomavirus variant is produced which has no cysteines in the sequence; the six cysteines of the wild type-protein (Cys-12, Cys-16, Cys-20, Cys-115, Cys-274 and Cys-283) are replaced by serine with the help of mutagenesis methods according to the state of the technology. This has among others the advantage that the redox conditions of the solution have no influence on the condition of the protein; therefore, it is easier to handle in many applications.

The mutagenesis is carried out by the QuickChange-method (Stratagene) according to the manufacturer's specification. The following oligonucleotides are used for the mutagenesis: C12S, C16S, C20S: 5'-GTC TCT AAA AGC GAG ACA AAA AGC ACA AAG GCT AGC CCA AGA CCC-3'(SEQ ID NO:1), and 5'-GGG TCT TGG GCT AGC CTT TGT GCT TTT TGT CTC GCT TTT AGA GAC-3' (SEQ ID NO:2), C115S: 5'-GAG GAC CTC ACG TCT GAC ACC CTA C-3'(SEQ ID NO:3) and 5'-GTA GGG TGT CAG ACG TGA GGT CCT C-3'(SEQ ID NO:4); C274S, C283S: 5'-GGG CCC TTC AGC AAA GGA GAA GGT CTA TAC CTC TCG AGC GTA GAT ATA ATG-3'(SEQ ID NO:5) and 5'-CAT TAT ATC TAC GCT CGA GAG GTA TAG ACC TTC TCC TTT GCT GAG GGG CCC-3'(SEQ ID NO:6).

Additionally, another protein can be produced that is deleted by 63 amino acids at the C-terminus. The C-terminus is essential for the assembly, the described variant of the coat protein is therefore assembly-deficient. The production of the shortened variant PyVP1-ΔCT63 is performed with the help of the oligonucleotide 5'-ATT ACC CGG GAT AGG GAT TTT TGA CCC ATC-3'(SEQ ID NO:7).

For the specific labelling of the capsomere, a singular cysteine can be introduced into a special region of the protein. This is, for example, the position 249, where a threonine is replaced by a cysteine. The mutagenesis is carried out with the QuickChange method (Stratagene) according to the manufacturer's specification, using the oligonucleotide 5'GGA CGG GTG GGG TGC ACG TGC GTG CAG TG-3' (SEQ ID NO:8) and 5'-CAC TGG AGG CAC GTG CAC CCC ACC CGT CC-3'(SEQ ID NO:9).

The assembly of the protein PyVp1-CallS-T249C, produced by standard methods, is first performed in analogy to the conditions already described in accordance to the state of the technology (cf. Salunke, Caspar & Garcea, *Biophys. J.* 56, S.887-900, 1989). Hereby, two assembly variants are used. The virus-like capsids with a diameter of 45 nm (consisting of 72 capsomeres), are obtained after dialysis of the protein against 10 mM HEPES, 50 mM NaCl, 0.5 mM $CaCL_2$, 5% glycerin, pH 7.2, after 72 hours at room temperature. On the other hand, much smaller particles (diameter 30 nm), consisting of 24 capsomeres, are formed by dialysis against 10 mM HEPES, 50 mM NaCl, 0.5 mM $CaCl_2$, 5% glycerin, pH 8.5, for 72 hours at room temperature.

The PyVP1-CallS-T249C protein in this experiment is expressed as a soluble pentamer and is native, meaning it is assembly-competent. In FIG. 2, a gel filtration experiment is shown which indicates that the PyVP1-CallS-T249C protein can be assembled under suitable condition to capsid-like structures of different sizes. FIG. 2 describes also the formed capsids with the help of electron-microscopical photographs.

The purified capsomeres can be labelled before assembly with the dyes Fluorescein-Maleimid or Texas Red-Maleimid (Molecular Probes) according to manufacturer's specification. Hereby, a specific coupling at the site of the singular cysteine 249 is carried out.

FIG. 3 shows the result of a FACS analysis of the assembled particles. In the FACS analysis the particles are surprisingly well detected, and they can also be distinguished

EXAMPLE 2

Characterization of the Aggregation of the Alzheimer β Peptide

The Alzheimer β peptide (1-42) in synthetic form is commercially sold by the company Sigma. The peptide is dissolved in a buffer containing 10 mM HEPES, 50 mM NaCl, and 2% SDS, pH 7.2. The peptide can be successfully fluorescence-labelled with the dye Rhodamin-X-succinimidylester (Molecular Probes) according to manufacturer's specifications at amino groups. Most of the excess dye can be separated afterwards from the peptide by a gel filtration column. The peptide labelled in this way (from fraction 3 of the gel filtration) is used in three parallel experiments. On the one hand, aggregation is induced by dilution (1:20) with an SDS-free buffer. The resulting aggregates can be detected with the help of the FACS method (FIG. 4A). If, as a control (experiment 2), it is diluted with SDS-containing buffer (2% SDS, w/v), no aggregates are formed and the specific FACS signals do not occur (FIG. 4B).

If, in the third experiment, SDS-free buffer is added, which additional contains unlabelled Alzheimer β peptide, then again, as expected, aggregates appear, however they show a minor fluorescence signal; clearly, unlabelled peptide has been built into the forming aggregates (which, according to the scattering curves, show a similar size distribution) (FIG. 4C).

As a control, the dissolved fluorescence dye (fraction 4 of the gel filtration) has also been measured (FIG. 4D), which does not provide a specific FACS signal in place of the Alzheimer β peptide (1-42) aggregate. The unlabelled peptide used as a control (FIG. 4E) likewise does not show a specific FACS signal.

This example demonstrates that size, type and composition of aggregates, consisting for instance of the Alzheimer β peptide, can be specifically characterized with the help of the FACS technology. Simultaneously, it is shown that unlabelled peptides of the same chemical nature, as for example occurring in liquor from patient, can be built into the amyloidogenic aggregates. Therefore, with this method the possibility to characterize molecular associates and aggregates highly sensitively and specifically has been demonstrated, characterizing pathological deposits.

EXAMPLE 3

Production and Characterization of Mixed Capsids

The characterization of mixed protein shells (capsids), i.e. particles build in a mosaic-like fashion from several different molecular substances, is a particularly elegant verification option of the present invention. In order to verify mixed capsids assembled from different coat proteins, onto the singular cysteine 249 of variant PyVP1-CallS-T249C of the coat protein (see example 1) in one experiment the fluorescence dye Fluorescein-Maleimide is coupled, and in a second experiment Texas Red-Maleimide. The differently labelled capsomeres are mixed and assembled with each other in an equimolar proportion. The analysis of the capsid formation is carried out by FACS. This makes the detection of different fluorescences within a single particle possible. FIG. 5 shows the analysis of capsids assembled under equimolar conditions. A population of fluorescence labelled capsids as well as of free non-assembled capsomeres is indicated (FIG. 5A, 5B). By graphing the Fluorescein-fluorescence against Texas Red-fluorescence, a population of particles is observed which carries both fluorescences at the same time. Particles labelled with only one dye, however, do not exist.

This example shows that the method described here allows the characterization of Polyomavirus VP1 coat proteins, assembling in a mosaic-like fashion, and it can be demonstrated that each single particle formed during the assembly has incorporated both differently fluorescence-labelled capsomere types. In contrast to to all other spectroscopic methods which measure an average of all existing fluorescences in the light beam, this method permits the determination of the distribution of the structure of molecular associates and aggregates on the basis of many individual particles. This makes it also possible apart from the characterization of individual particles to determine the statistical distribution of the subunits, built into each particle, if these have been labelled with different fluorescence dyes.

The invention claimed is:

1. A method for characterizing in a sample molecular associates consisting of subunits, comprising the steps of:
   (1) labeling non-associated subunits directly with at least one fluorescence dye,
   (2) contacting the labeled subunits with the sample, under conditions that permit the association and/or binding of the labeled subunits to each other, to reach an association and/or binding of the labeled subunits to each other or to unlabeled subunits present in the sample or to molecular associates present in the sample, and to form labeled molecular associates, and
   (3) determining size, granularity, or fluorescence of the labeled molecular associates by a FACS (Fluorescence-Activated Cell Sorter), thereby distinguishing (a) the labeled molecular associates formed by the labeled subunits with each other from (b) the labeled molecular associates formed by the labeled subunits with unlabeled subunits present in the sample or (c) the labeled molecular associates formed by the labeled subunits with the molecular associates present in the sample,
wherein the molecular associates are virus or phage capsids, proteasomes, chaperon complexes, or ribosomes, or are built up from modified subunits thereof, or are peptide associates or protein associates comprising a peptide, a protein, a glycoprotein, or a lipoprotein, and wherein the molecular associates do not comprise cells.

2. The method according to claim 1, wherein the subunits are monomers, dimers and/or oligomers.

3. The method according to claim 1, wherein the subunits of the molecular associates are identical or differ from each other.

4. The method according to claim 1, further comprising step (4) of separating the molecular associates according to their size, granularity, or fluorescence.

5. The method according to claim 1, wherein the molecular associates are virus capsids or phage capsids of the group of Adenoviridae, Arenaviridae, Arterivirus, Astroviridae, Bacilloviridae, Baculoviridae, Batnavirus, Bamaviridae, Bimaviridae, Bromoviridae, Bunyaviridae, Caliciviridae, Capillovirus, Carlavirus, Caulimovirus, Circoviridae, Closterovirus, Comoviridae, Coronaviridae, Corticoviridae, Cystoviridae, Dianthovirus, Enamovirus, Filoviridae, Flaviviridae, Furovirus, Fuselloviridae, Geminiviridae, Guttaviridae, Hepadnaviridae, Herpesviridae, Hordeivirus, Hypoviridae, Idaeovirus, Inoviridae, Iridoviridae, Leviviridae, Lipothrixviridae, Luteovirus, Machlomovirus, Marafivirus, Microviridae, Myoviridae, Necrovirus, Nodaviridae, Orthomyxoviridae, Papovaviridae, Paramyxoviridae, Partitiviridae, Parvoviridae, Phycodnaviridae, Picomaviridae, Plasmaviridae, Podoviridae, Polydnaviridae, Potexvirus, Potyviridae, Poxviridae, Reoviridae, Retroviridae, Rhabdoviridae, Rhizidiovirus, Sequiviridae, Siphoviridae, Sobemovirus, Tectiviridae, Tenuivirus, Tetraviridae, Tobamovirus, Tobravirus, Togaviridae, Tombusviridae, Totiviridae, Trichovirus, Tymovirus, Umbravirus or are from the same or are from one or more modified subunits of the mentioned viruses or phages.

6. The method according to claim 1, wherein the subunits of the molecular associates are Alzheimer-β-peptides, tau proteins, prion proteins, huntingtin, synuclein, SCA1/ ataxin 1, cystatin C, immunoglobulins, lipoproteins, transthyretin, apoliproprotein A1, serum amyloid A, islet amyloid polypeptide, insulin, calcitonin, β-2-microglobulin, lysozyme, fibrinogen, gelsolin, atrial natriuretic factor, transcription factor CBFA1, poly(A)-binding protein II, or are modified forms or fragments thereof.

7. The method according to claim 6, wherein said molecular associates appear during the neurodegenerative diseases Morbus Alzheimer, Transmissible Spongiform Encephalopathy, Chorea Huntington, Morbus Parkinson, Spinocerebellar Ataxia Type 1, and Hereditary Cerebral Amyloid Angiopathy or during the diseases Primary or Reactive Asystemic Amyloidosis, Secondary Systemic Amyloidosis, Familial Amyloid Polyneuropathy I and III, Diabetes Mellitus Type II, Injection-localized and Dialysis-associated Amyloidosis, Medullary Carcinoma of the thyroid, β-2-Microglobulin Amyloidosis, Non-Neuropathic Amyloidosis, Inherited Renal Amyloidosis, Finnish Inherited Systemic Amyloidosis, Atrial Amyloidosis, Syndactuly Type II, Machado-Josephs Disease, Cleidocranialic Dysplasy and Ocular-pharyngitic Myodystrophy.

* * * * *

SEQUENCE LISTING

```
<160> NUMBER OF SEQ ID NOS: 9

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:C12S, C16S,
      C20S mutagenesis oligonucleotide

<400> SEQUENCE: 1
gtctctaaaa gcgagacaaa aagcacaaag gctagcccaa gaccc              45

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence:C12S, C16S,
```

```
            C20S mutagenesis oligonucleotide

<400> SEQUENCE: 2
gggtcttggg ctagcctttg tgcttttgt ctcgctttta gagac              45

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:C115S
      mutagenesis oligonucleotide

<400> SEQUENCE: 3
gaggacctca cgtctgacac cctac                                   25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:C115S
      mutagenesis oligonucleotide

<400> SEQUENCE: 4
gtagggtgtc agacgtgagg tcctc                                   25

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence:C274S, C283S
      mutagenesis oligonucleotide

<400> SEQUENCE: 5
gggcccttca gcaaaggaga aggtctatac ctctcgagcg tagatataat g       51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence:C274S, C283S
      mutagenesis oligonucleotide

<400> SEQUENCE: 6
cattatatct acgctcgaga ggtatagacc ttctcctttg ctgaggggcc c       51

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      oligonucleotide for production of C-terminus shortened variant
      PyVP1-deltaCT63

<400> SEQUENCE: 7
attacccggg atagggattt ttgacccatc                              30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:mutagenesis
```

```
                                       -continued oligonucleotide for position 249 Thr replaced by Cys

<400> SEQUENCE: 8
ggacgggtgg ggtgcacgtg cgtgcagtg                                          29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:mutagenesis
      oligonucleotide for position 249 Thr replaced by
      Cys

<400> SEQUENCE: 9
cactggaggc acgtgcaccc cacccgtcc                                          29
```